United States Patent [19]

Orr

[11] 4,331,609

[45] May 25, 1982

[54] ANTIPERSPIRANT COMPOSITION

[75] Inventor: Thomas V. Orr, Cincinnati, Ohio

[73] Assignee: The Procter & Gamble Company, Cincinnati, Ohio

[21] Appl. No.: 184,862

[22] Filed: Sep. 8, 1980

[51] Int. Cl.$^3$ .............................................. C07F 5/06
[52] U.S. Cl. ................................. 260/448 R; 424/66
[58] Field of Search ................ 424/68, 66; 260/429.3, 260/429 R

[56] References Cited

U.S. PATENT DOCUMENTS

| | | | |
|---|---|---|---|
| 2,814,584 | 11/1957 | Daley | 424/66 |
| 2,814,585 | 11/1957 | Daley | 424/66 |
| 2,854,382 | 9/1958 | Grad | 424/66 |
| 3,009,771 | 11/1961 | Grote | 424/66 X |
| 3,407,254 | 10/1968 | Siegal et al. | 424/66 |
| 3,792,068 | 2/1974 | Luedders et al. | 260/429.3 |
| 3,903,258 | 9/1975 | Siegel | 424/66 |
| 3,998,788 | 12/1976 | Rubino | 260/429.3 |
| 4,017,559 | 4/1977 | Rubino | 424/47 |
| 4,021,536 | 5/1977 | Rubino | 260/429.3 |
| 4,028,390 | 6/1977 | Rubino et al. | 260/429.3 |

FOREIGN PATENT DOCUMENTS 1487812 10/1977 United Kingdom .

Primary Examiner—Helen M. S. Sneed
Attorney, Agent, or Firm—Monte D. Witte; Douglas C. Mohl; Richard C. Witte

[57] ABSTRACT

Antiperspirant compositions comprising aluminum and zirconium. Efficacious, aqueous solution-stable, antiperspirant complexes comprise an aluminum compound, a zirconium compound, a water soluble neutral amino acid, and an inorganic acidic compound. The aluminum compound is an aluminum chlorohydrate having an aluminum to chlorine molar ratio of from about 1.60 to about 2.5 while the zirconium compound is a zirconyl hydroxychloride having a zirconium to chlorine molar ratio of from about 0.67 to about 2.0. In the antiperspirant complex, the aluminum to zirconium molar ratio is from about 2 to about 10, the total metal to chlorine molar ratio is less than about 1.30, and the neutral amino acid to total metal molar ratio is from about 0.09 to about 0.24. The neutral amino acid to total metal molar ratio is from about 0.09 to about 0.75 when the antiperspirant complex is used in non-aqueous systems.

31 Claims, No Drawings

ANTIPERSPIRANT COMPOSITION

BACKGROUND OF THE INVENTION

1. Technical Field of the Invention

This invention relates to antiperspirant compositions. More particularly, this invention relates to highly effective aluminum-zirconium antiperspirant complexes which are non-irritating to the skin and which are non-damaging to textiles.

2. Background Art

Cosmetic preparations having a perspiration inhibiting or retarding effect are well known, and many chemical compounds capable of preventing or retarding the exudation of perspiration have been used or suggested for use in such preparations. In recent years, complexes comprising aluminum and zirconium have been widely used.

Workers such as Grad in U.S. Pat. No. 2,854,382 (issued Sept. 30, 1958) and Daley in U.S. Pat. No. 2,814,585 (issued Nov. 26, 1957), both of which are incorporated herein by reference, describe the use of aluminum chlorohydroxide and either zirconium oxychloride or zirconyl hydroxychloride in combination with an amino acid as the active component of antiperspirant formulations.

Grad, for example, taught that an active antiperspirant complex comprises three necessary components. The first component is zirconyl hydroxychloride, a complex compound having the empirical formula ZrO(OH)Cl. The second necessary component is aluminum chlorohydroxide, a complex compound having the empirical formula $Al_2(OH)_{6-r}Cl_r$ wherein r has an average value of from about 0.8 to about 1.2. The third necessary component is a water-soluble neutral amino acid, i.e. an acid wherein the number of amino groups equals the number of carboxyl groups.

Schmitz, in Belgian Pat. No. 153,023 (issued Aug. 4, 1975) incorporated herein by reference, also teaches aluminum-zirconium antiperspirant complexes, but complexes which are somewhat different from those taught by Grad. Like Grad, Schmitz uses aluminum chlorohydroxide having the empirical formula $Al_2(OH)_{6-r}Cl_r$, wherein r has an average value of from about 0.8 to about 1.2. Schmitz's complex differs from Grad's in that Schmitz uses a novel zirconium compound having the empirical formula $ZrO(OH)_{2-p}Cl_p$ wherein p has an average value of from about 1.50 to about 1.87. Because its pH is somewhat lower than that of the more common zirconyl hydroxychloride, Schmitz's novel material is sometimes called acid zirconyl hydroxychloride, or acid ZHC. Schmitz's antiperspirant complex comprises from 0.15 to 1.5 parts by weight acid ZHC, 1 part ACH, and from about 0.06 to about 60 parts neutral amino acid such as glycine.

While both Grad and Schmitz teach effective antiperspirant complexes, materials having greater effectiveness are still sought. Further, one important use of antiperspirant complexes is in liquid ("roll-on") cosmetic products. The Schmitz complexes exhibit certain physical instabilities when presented in aqueous preparations which make their use in such products less than optimum. This instability is manifested by an increase in viscosity of the aqueous preparations over relatively short periods of time. In fact, this increase in viscosity has, in some cases, been so dramatic that gels are formed. This instability has limited the practical use of such antiperspirant complexes to preparations wherein the presence of a gel can be tolerated (i.e. creams, powders, etc.).

It is an object of this invention to provide novel aluminum and zirconium complexes which are effective antiperspirant materials (i.e. which are highly effective in inhibiting or retarding the exudation of perspiration) and which are stable in aqueous solution while being non-irritating to skin and non-damaging to textiles, and which do not adversely affect containers.

It is a further object of this invention to provide processes for making the novel antiperspirant complexes of this invention.

It is a still further object of this invention to provide cosmetically attractive antiperspirant preparations comprising the novel antiperspirant complexes of this invention.

Other objects will become readily apparent from a reading of the following detailed disclosure of this invention.

SUMMARY OF THE INVENTION

According to the present invention, it has been found that efficacious antiperspirant complexes can be obtained by forming a water-soluble, stable complex comprising a combination of an aluminum compound, a zirconium compound, a neutral amino acid, and an inorganic acidic compound.

DETAILED DESCRIPTION OF THE INVENTION

While this specification concludes with claims particularly pointing out and distinctly claiming that which is considered to be the subject matter of this invention, it is believed that the invention as a whole will be more readily understood through a careful reading of the following detailed description.

This invention relates to antiperspirant aluminum and zirconium complexes comprising an aluminum compound, a zirconium compound, a neutral amino acid, and an inorganic acidic compound.

The first component of the complexes is an aluminum compound which has the empirical formula $Al_2(OH)_{6-n}X_n$ wherein n has a value of from about 0.80 to about 1.25 and X is selected from the group consisting of chlorine, bromine, iodine, sulfamate, sulfate, nitrate, and mixtures thereof. In the preferred embodiments of this invention, and in usual commercial practice generally in the antiperspirant art, the aluminum compound is a chloride salt. For convenience, this invention will be discussed hereinafter in terms of the chloride salts of the aluminum compound, $Al_2(OH)_{6-n}Cl_n$, which will be referred to as aluminum chlorohydroxide or ACH.

As used in this invention, the aluminum chlorohydrate should have an aluminum to chlorine molar ratio of from about 1.60 to about 2.5, preferably about 2.0. Preferably, n in the empirical formula is about 1. In the preferred case, the aluminum chlorohydrate is $Al_2(OH)_5Cl$, which is sometimes referred to in the trade as 5/6 basic aluminum chloride. Mixtures of more than one particular aluminum chlorohydrate can be used in this invention so long as the overall molar ratios are maintained as recited above. Aluminum chlorohydrates are staple items of commerce.

The second component of the complexes is a zirconium compound which has the empirical formula $ZrO(OH)_{2-m}Y_m$ wherein m has a value of from about 0.50 to about 1.5 and Y is selected from the group consisting of chlorine, bromine, iodine, and mixtures thereof. In the preferred embodiments of this invention, and in usual commercial practice generally in the antiperspirant art, the zirconium compound is a chloride salt. For convenience, this invention will be discussed hereinafter in terms of the chloride salts of the zirconium compound, $ZrO(OH)_{2-m}Cl_m$, which will be referred to as zirconium hydroxychloride or ZHC.

Heretofore and hereinafter in this specification, the antiperspirant complexes of this invention have been and will be referred to as aluminum and zirconium complexes and the second component thereof as a zirconium compound. Zirconium is the preferred metal and the metal normally used is usual commercial practice. It is to be understood, however, that hafnium and mixtures of hafnium and zirconium can be substituted for zirconium without departing from the scope and spirit of this invention. Formally, then, the second component of the antiperspirant complexes of this invention has the empirical formula $DO(OH)_{2-m}Y_m$ wherein D is selected from the group consisting of zirconium, hafnium, and mixtures thereof; m has a value of from about 0.50 to about 1.5; and Y is selected from the group consisting of chlorine, bromine, iodine, and mixtures thereof.

The zirconium hydroxychloride used in this invention must be non-acid zirconium hydroxychloride. That is, the molar ratio of zirconium to chlorine must be from about 0.67 to about 2.0. Preferably, the ratio is about 1.0. In the general empirical formula, m is preferably 1.0. These zirconium compounds are commercially available in the form of aqueous solutions. Alternatively, they can be prepared by dissolving a preselected quantity of zirconyl carbonate paste, which is commercially available, in the corresponding amount of an appropriate acid, such as hydrochloride acid. Mixtures of more than one zirconium hydroxychloride can be used in this invention so long as each particular species falls within the scope of the above teaching.

The third component of the complexes is an amino acid which is a water soluble neutral amino acid. A neutral amino acid is one in which the number of amino groups in the molecule is equal to the number of carboxyl groups in the molecule. The most preferred amino acid is glycine. Other suitable amino acids are alanine, β-alanine, methionine, tryptophan, β-phenylalanine, serine, valine, and 2-amino-butyric acid.

The fourth component of the complexes is an inorganic acidic compound selected from the group consisting of aluminum chloride, hydrochloric acid, and mixtures thereof. Hydrochloric acid (sometimes referred to in the older literature as muriatic acid) is a staple item of commerce. It can be used in either concentrated form or diluted. Aluminum chloride ($AlCl_3$) is, likewise, a staple item of commerce. Either the anhydrous form or the hexahydrate ($AlCl_3.6H_2O$) form can be used. Preferably, the hexahydrate is dissolved in the aqueous solution of aluminum chlorohydrate used in the preparation of the antiperspirant complexes of this invention.

One preparing the antiperspirant complexes of this invention can prepare, or have prepared, or obtain in prepared form, a premix of aluminum chlorohydrate and $AlCl_3$ or HCl. This premix is handled as a unit and can be used in the making of the antiperspirant complex of this invention as a partial or total replacement for the aluminum chlorohydrate and inorganic acidic compound used separately as described above. Further, one can, without departing from the scope and spirit of this invention, prepare the antiperspirant complexes of this invention by mixing any convenient chemical compounds containing aluminum and anions selected from the group consisting of chlorine, bromine, iodine, and mixtures thereof, with a compound having the empirical formula $DO(OH)_{2-m}Y_m$ as defined above, and with a water soluble neutral amino acid so long as the antiperspirant complex so prepared has the molar ratios discussed below. Preferably, D is zirconium and Y is chlorine as is the anion associated with the aluminum.

Polyvalent elements such as aluminum and zirconium are capable of forming polymeric compounds or complexes. In fact, compounds containing these elements are generally polymeric when in aqueous solution. The compounds used in forming the complexes of this invention are described and discussed in this specification in terms of their empirical formulae. It is to be understood that this is merely a convenient way of describing a complex molecule which may have a widely varying composition and molecular weight. For example, the recited empirical formula for aluminum chlorohydrate is greatly simplified in that the aluminum compounds used in this invention can combine in complicated ways to form various polymers with and without bound molecules of water.

The novel antiperspirant complex should have an aluminum to zirconium molar ratio of from about 2 to about 10. Preferably, this ratio should be from about 2.5 to about 7, and most preferably from about 2.5 to about 4.5. As indicated supra, this invention is being discussed, for convenience, in terms of a complex comprising zirconium. Formally, the ratio discussed in this paragraph is the ratio of aluminum to non-aluminum (i.e. zirconium, hafnium, and mixtures thereof) metal in the complex.

The molar ratio of total metal in the antiperspirant complex (i.e. the total aluminum and zirconium in the antiperspirant complex) to the chlorine in the complex must be less than about 1.30. The efficacy of the antiperspirant complex decreases precipitously as the molar ratio of total metal to chlorine increases from about 1.30 to about 1.4. While the efficacy of the antiperspirant complex is relatively constant as the molar ratio of total metal to chlorine decreases from about 1.30, the skin irritation properties of the complex increase as this ratio decreases below about 0.80. Preferably, the molar ratio of total metal to chlorine in the antiperspirant complex is from about 0.80 to about 1.25. As indicated supra, this invention is being discussed, for convenience, in terms of chloride salts. Formally, the ratio discussed in this paragraph is the ratio of total metal to total non-hydroxy anion in the antiperspirant complex of this invention.

The exact quantities of aluminum chlorohydrate and zirconium hydroxychloride and inorganic acidic compound which are used in forming the complex of this invention depend upon the specific materials selected for use therein as well as the molar ratios selected for use.

The neutral amino acid should be present in the antiperspirant complex in such an amount that the molar ratio of neutral amino acid to total metal is from about 0.09 to about 0.24, preferably about 0.13 to about 0.20, to provide a complex stable in aqueous solution.

In the most preferred embodiment of the antiperspirant complex of this invention, the molar ratio of total metal to chlorine is 1.25; of aluminum to zirconium, 3.3; of glycine to total metal, 0.18; and of zirconium to chlorine in the zirconyl hydroxy chloride, 1.00.

To make the antiperspirant complexes of this invention, the final aluminum to zirconium and total metal to chlorine molar ratios are selected in accordance with the principles hereinbefore disclosed. Then, the particular aluminum chlorohydroxide, zirconium hydroxychoride, neutral amino acid, and inorganic acidic compound are selected in accordance with the principles hereinbefore disclosed. The particular compounds are selected on the basis of convenience, cost, and availability. The appropriate amounts of each of the selected compounds can then, of course, be readily calculated by simple material balance. The components of the complex are then mixed in water at any convenient temperature below about 140° C., preferably room temperature. The order of mixing is immaterial. Preferably, the total solids content of the resulting aqueous solution is from about 32 to about 38% by weight, exclusive of the neutral amino acid present.

The antiperspirant complexes of this invention are formulated into cosmetic preparations having perspiration inhibiting or retarding effects. These cosmetic preparations usually contain, in addition to the antiperspirant complex of this invention, various auxillary materials which enhance the aesthetic characteristics of the formulation. Included among these auxilliary materials are, without limitation, perfumes, dyes, pigments, emollients, thickening agents, etc. The only requirement for the selection of the auxilliary materials is that they do not adversely interact with the antiperspirant complexes of this invention. In general, it has been found that the materials commonly used in cosmetic formulations do not so adversely interact.

It is anticipated that the antiperspirant complexes of this invention will be used principally in lotion or "roll-on" cosmetic preparations inasmuch as the stability in aqueous solution of the antiperspirant complex of this invention is far superior to the stability of other such complexes. When used in this lotion form, the total level of antiperspirant complex in the lotion preparation is preferably from about 17% to about 23% by weight exclusive of the neutral amino acid present.

The antiperspirant complexes of this invention can also be used in other types of cosmetic preparations such as creams, sticks, powders, and the like. In these types of cosmetic preparations stability in aqueous solution is of little moment in that stability in aqueous solution of from about one to about five days is sufficient to allow for economical processing. The amount of neutral amino acid present in the antiperspirant complexes of the present invention used in such types of preparations should then be such that the molar ratio of neutral amino acid to total metal is from about 0.09 to about 0.75, preferably from about 0.09 to about 0.40. When used in cream, stick, or powder form, the total level of antiperspirant complex is preferably from about 17% to about 23% by weight exclusive of neutral amino acid present.

The antiperspirant complexes of this invention can optionally be dried by any of the techniques commonly used by those skilled in the art. If they are dried, the antiperspirant complexes is essentially solid form can either be redissolved in an aqueous medium prior to use in a lotion-type cosmetic preparation or be used directly in the dried form in another type of cosmetic preparation.

One of the significant advantages of this invention is the enhanced stability of the antiperspirant complexes of this invention in aqueous solution. It was noted above that polyvalent compounds are generally present, in aqueous solution, as polymeric or complex molecules. The antiperspirant complexes of this invention are no exception. However, the antiperspirant complexes of this invention do not polymerize rapidly in aqueous solution thereby maintaining relatively low viscosities and not forming gels. Unless otherwise indicated, stability, as used herein, refers to the property of a system which allows it to maintain essentially its initial viscosity for an extended period of time, at least about 45 days, at temperatures commonly encountered by antiperspirant cosmetic preparations.

Viscosities are measured in the usual manner with a Brookfield viscosimeter with a number 2 spindle at 25° C.

The efficacy of antiperspirant complexes, or of cosmetic antiperspirant preparations, is determined by measuring the difference in amount of perspiration exuded from the axillae of test subjects under standard conditions without and with the use of the material under study. Alternatively, the efficacy of a material can be determined by measuring the difference in amount of perspiration exuded when the test subject uses a standard (or control) antiperspirant preparation and when he uses the material under study. Any accurate, reproducible test can be used. An example of such a test is found in Majois et al, J. Soc. Cosmet. Chem., 25, 139–152 (March 1974) which is incorporated herein by reference.

In order to more fully and completely describe the present invention, the following specific, non-limiting examples are presented. Unless otherwise specified, hereinafter in this specification all ratios are molar ratios, all percentages are weight percentages, all parts are parts by weight, and M represents total metal content.

EXAMPLE I

An antiperspirant complex of this invention (Complex I) having the following composition was prepared:

| COMPLEX I | |
|---|---|
| M:Cl | 1.2 |
| Al:Zr | 3.3 |
| Zr:Cl (in ZHC) | 1.0 |
| Glycine:M | 0.18. |

Complex I was prepared by mixing at ambient temperature:

| ACH | 663 parts |
|---|---|
| ZHC | 693 parts |
| Glycine | 60 parts |
| $AlCl_3 \cdot 6H_2O$ | 84 parts. |

As used in preparing Complex I, the ACH was nominally a 50% aqueous solution of 5/6 basic aluminum chloride, $Al_2(OH)_5Cl$, and the ZHC was an aqueous solution of a compound having the empirical formula $ZrO(OH)Cl$. Analyses of the components showed them to have the following compositions:

| ACH | 12.7% Al and 8.0% Cl |
|---|---|
| ZHC | 13.8% Zr and 5.6% Cl |
| $AlCl_3 \cdot 6H_2O$ | 11.3% Al and 43.6% Cl. |

Complex I was a stable, efficacious antiperspirant complex. In order to demonstrate its efficacy, it was compared to a prior art aluminum and zirconium antiperspirant complex (Control A) made essentially according to the teachings of Grad supra. This Control A complex, which is itself an efficacious antiperspirant complex, had the composition:

| CONTROL A | |
|---|---|
| M:Cl | 1.63 |
| Al:Zr | 3.3 |
| Zr:Cl (in ZHC) | 1.0 |
| Glycine:M | 0.29. |

Control A was prepared by mixing

| ACH | 487 parts |
|---|---|
| ZHC | 446 parts |
| Glycine | 67 parts |

In this case, the components used to make the Control were nominally the same as those used to make Complex I, but had the following actual analyses:

| ACH | 12.6% Al and 8.1% Cl |
|---|---|
| ZHC | 14.1% Zr and 5.6% Cl. |

Complex I was shown to reduce exudation of perspiration by 28% as compared to Control A.

EXAMPLES II AND III

As indicated supra, it has been discovered that the efficacy of an antiperspirant complex decreases as the molar ratio of total metal to chlorine increases from about 1.30 to about 1.4. To demonstrate this phenomenon, antiperspirant complexes having the following compositions were prepared:

| | COMPLEX II | COMPLEX III |
|---|---|---|
| M:Cl | 1.30 | 1.35 |
| Al:Zr | 3.3 | 3.3 |
| Zr:Cl (in ZHC) | 1.0 | 1.0 |
| Glycine:M | 0.17 | 0.17. |

These two complexes were prepared by mixing:

| | COMPLEX II | COMPLEX III |
|---|---|---|
| ACH | 694 parts | 706 parts |
| ZHC | 673 parts | 673 parts |
| Glycine | 60 parts | 60 parts |
| AlCl$_3$ . 6H$_2$O | 72 parts | 60 parts |

The components used to make Complexes II and III had the following actual analyses:

| ACH | 12.7% Al and 8.0% Cl |
|---|---|
| ZHC | 14.7% Zr and 5.9% Cl |
| AlCl$_3$ . 6H$_2$O | 11.3% Al and 43.9% Cl. |

Complex II, which is an example of an antiperspirant complex of this invention, reduced perspiration exudation by 13% compared to Control B (a prior art aluminum and zirconium complex described below) while Complex III reduced perspiration exudation by only 2%. The former value represents a statistically significant improvement over the Control while the latter value is, statistically, no different from the Control.

| CONTROL B | |
|---|---|
| M:Cl | 1.63 |
| Al:Zr | 3.3 |
| Zr:Cl (in ZHC) | 1.0 |
| Glycine:M | 0.29. |

Control B was prepared by mixing

| ACH | 742 parts |
|---|---|
| ZHC | 658 parts |
| Glycine | 100 parts |

The ACH and ZHC were the same as used in Complexes II and III.

EXAMPLES IV THROUGH XI

The following complexes, Complex IV through Complex XI, are further examples of the antiperspirant complexes of this invention.

| | COMPLEX NUMBER | | | | | | | |
|---|---|---|---|---|---|---|---|---|
| | IV | V | VI | VII | VIII | IX | X | XI |
| M:Cl | 1.2 | 1.2 | 1.2 | 1.2 | 0.8 | 1.2 | 1.2 | 1.2 |
| Al:Zr | 3.3 | 3.3 | 3.3 | 3.3 | 3.3 | 2.5 | 9.0 | 7.0 |
| Glycine:M | 0.17 | 0.17 | 0.17 | 0.17 | 0.13 | 0.19 | 0.14 | 0.15 |
| Zr:Cl (in ZHC) | 0.67 | 2.0 | 1.0 | 1.0 | 1.0 | 1.0 | 1.0 | 1.0 |
| Al:Cl (in ACH) | 2.0 | 2.0 | 1.6 | 2.5 | 2.0 | 2.0 | 2.0 | 2.0 |

The ACH having an Al:Cl ratio of 2.0 has the empirical formula Al$_2$(OH)$_5$Cl and is present in an aqueous solution having 12.7% Al and 8.0% Cl. That having an Al:Cl ratio of 1.6 is, empirically, Al$_2$(OH)$_{4.75}$Cl$_{1.25}$ and is present in an aqueous solution having 12.7% Al and 10.4% Cl. That having an Al:Cl ratio of 2.5 is, empirically, Al$_2$(OH)$_{5.2}$Cl$_{0.8}$ and is present in an aqueous solution having 12.7% Al and 6.7% Cl.

The ZHC having a Zr:Cl ratio of 0.67 has the empirical formula ZrO(OH)$_{0.5}$Cl$_{1.5}$ and is present in an aqueous solution having 14.3% Zr and 8.3% Cl. That having a Zr:Cl ratio of 2.0 is, empirically, ZrO(OH)$_{1.5}$Cl$_{0.5}$ and is present in an aqueous solution having 14.3% Zr and 2.8% Cl. That having a Zr:Cl ratio of 1.0 is, empirically, ZrO(OH)Cl and is present in an aqueous solution having 14.3% Zr and 5.6% Cl.

The AlCl$_3$.6H$_2$O has 11.2% Al and 44.1% Cl.

The complexes are formed by mixing, at room temperature, the following materials:

| | COMPLEX NUMBER | | | |
|---|---|---|---|---|
| | IV | V | VI | VII |
| ACH (Al:Cl = 1.6) | X | X | 46.7 | X |
| ACH (Al:Cl = 2.0) | 47.0 | 40.7 | X | X |
| ACH (Al:Cl = 2.5) | X | X | X | 42.4 |
| ZHC (Zr:Cl = 0.67) | 45.5 | X | X | X |
| ZHC (Zr:Cl = 1.0) | X | X | 45.5 | 45.3 |
| ZHC (Zr:Cl = 2.0) | X | 45.2 | X | X |
| AlCl$_3$ . 6H$_2$O | 3.5 | 10.2 | 3.8 | 8.3 |
| Glycine | 4.0 | 4.0 | 4.0 | 4.0 |

|  | COMPLEX NUMBER | | | |
|---|---|---|---|---|
|  | VIII | IX | X | XI |
| ACH (Al:Cl = 2.0) | 33.0 | 38.4 | 61.6 | 57.7 |
| ZHC (Zr:Cl = 1.0) | 45.1 | 52.0 | 23.7 | 28.5 |
| AlCl$_3$ . 6H$_2$O | 18.9 | 5.6 | 10.7 | 9.9 |
| Glycine | 3.0 | 4.0 | 4.0 | 4.0 |

The resulting antiperspirant complexes are stable and efficacious.

When the glycine in Complex I and Complexes IV through XI is replaced on a molar basis with alanine, β-alanine, methionine, trytophan, β-phenyl-alamine, serine, valine, and 2-amino-butyric acid, stable efficacious antiperspirant complexes result.

When the AlCl$_3$.6H$_2$O in Complex I and Complexes IV through IX is replaced by hydrochloric acid and the levels of the other components are adjusted on the basis of material balances to maintain the recited ratios constant, stable and efficacious antiperspirant complexes result.

EXAMPLE XII

A cosmetically attractive, lotion ("roll-on") antiperspirant preparation is prepared by mixing the following materials:

| Complex I | 63 parts |
|---|---|
| C-25 parafin wax | 1.8 |
| Isopropylpalmitate | 1.8 |
| Glycerol monostearate | 4.1 |
| Polyoxyethylene stearate | 6.4 |
| Water | 18.9 |
| Bentonite clay | 1.0 |
| Glycerine | 3.0 |

EXAMPLE XIII

Complex I is spray dried and the active powder thus obtained is used in the following stick-type antiperspirant preparation:

| Complex I (active powder) | 26.7 parts |
|---|---|
| Silicone 7158 | 44.0 |
| Fluid AP | 5.0 |
| Stearyl alcohol | 11.5 |
| Castor Wax MP80 | 5.0 |
| Talc | 7.0 |
| Perfume | 0.8 |

Silicone 7158 is a cyclomethicone made by Union Carbide Corp., New York, N.Y. Fluid AP is a butyl ether also made by Union Carbide. Castor Wax MP80 is a naturally occuring wax having a melting point of 80° C.

What is claimed is:

1. An antiperspirant complex comprising:
   (a) as a first component, Al(OH)$_{6-n}$X$_n$ wherein n has a value of from about 0.80 to about 1.25 and X is selected from the group consisting of chlorine, bromine, iodine, sulfamate, sulfate, nitrate, and mixtures thereof;
   (b) as a second component, DO(OH)$_{2-m}$Y$_m$ wherein m has a value of about 1.0, D is selected from the group consisting of zirconium, hafnium, and mixtures thereof, and Y is selected from the group consisting of chlorine, bromine, iodine, and mixtures thereof;
   (c) as a third component, a water soluble neutral amino acid; and
   (d) as a fourth component, an inorganic acidic compound selected from the group consisting of aluminum chloride, hydrochloric acid, and mixtures thereof, wherein the molar ratio of total metal to non-hydroxy anion in said antiperspirant complex is less than about 1.3, the molar ratio of aluminum to non-aluminum metal in the complex is from about 2 to about 10, and the molar ratio of neutral amino acid to total metal in the complex is from about 0.09 to about 0.24.

2. The complex of claim 1 wherein the molar ratio of aluminum to non-aluminum metal in the complex is from about 2.5 to about 7.

3. The complex of claim 1 wherein the molar ratio of aluminum to non-aluminum metal in the complex is from about 2.5 to about 4.5.

4. The complex of claims 1, 2 or 3 wherein the molar ratio of total metal to non-hydroxy anion in the complex is from about 0.8 to about 1.25.

5. The complex of claim 1 wherein n is about 1, the molar ratio of aluminum to non-aluminum metal in the complex is from about 2.5 to about 4.5, and the molar ratio of total metal to non-hydroxy anion in the complex is from 0.8 to about 1.25.

6. The complex of claim 1 wherein m is about 1, the molar ratio of aluminum to non-aluminum metal in the complex is from about 2.5 to about 4.5 and the molar ratio of total metal to non-hydroxy anion in the complex is from about 0.8 to about 1.25.

7. The complex of claim 1 wherein n is about 1, the molar ratio of aluminum to non-aluminum metal in the complex is from about 2.5 to about 4.5 and the molar ratio of total metal to non-hydroxy anion in the complex is from about 0.8 to about 1.25.

8. The complex of claims 1, 2, 3, 5, 6, or 7 wherein D is zirconium, X is chlorine and Y is chlorine.

9. The complex of claims 1, 2, or 3 wherein D is zirconium, X is chlorine, Y is chlorine and the molar ratio of total metal to chlorine in the complex is from about 0.8 to about 1.25.

10. The complex of claims 1, 2, 3, 5, 6, or 7, wherein said water soluble neutral amino acid is glycine.

11. The complex of claim 4 wherein said water soluble neutral amino acid is glycine.

12. The complex of claim 8 wherein said water soluble neutral amino acid is glycine.

13. The complex of claim 9 wherein said water soluble neutral amino acid is glycine.

14. An antiperspirant complex comprising aluminum; a non-aluminum metal selected from the group consisting of zirconium, hafnium, and mixtures thereof; an anion selected from the group consisting of chlorine, bromine, iodine, and mixtures thereof; and a water soluble neutral amino acid wherein the molar ratio of total metal to said anion is less than about 1:3; the molar ratio of aluminum to non-aluminum metal is from about 2 to about 10; and the molar ratio of water soluble neutral amino acid to total metal is from about 0.09 to about 0.24; wherein said non-aluminum metal is incorporated into the antiperspirant complex in the form of a compound having the empirical formula DO(OH)$_{2-m}$Y$_m$ wherein m has a value of about 1.0, D is selected from the group consisting of zirconium, hafnium, and mixtures thereof, and Y is selected from the group consisting of chlorine, bromine, iodine, and mixtures thereof.

15. The complex of claim 14 wherein the molar ratio of aluminum to non-aluminum metal is from about 2.5 to about 4.5.

16. The complex of claims 14 or 15 wherein the molar ratio of total metal to said anion is from about 0.8 to about 1.25.

17. The complex of claims 14 or 15 wherein said non-aluminum metal and D are both zirconium and wherein said anion and Y are both chlorine.

18. The complex of claim 16 wherein said non-aluminum metal and D are both zirconium and wherein said anion and Y are both chlorine.

19. The complex of claims 14 or 15, wherein said water soluble neutral amino acid is glycine.

20. The complexes of claim 16 wherein said water soluble neutral amino acid is glycine.

21. The complex of claim 17 wherein said water soluble neutral amino acid is glycine.

22. The complex of claim 18 wherein said water soluble neutral amino acid is glycine.

23. An antiperspirant complex comprising aluminum; a non-aluminum metal selected from the group consisting of zirconium, hafnium, and mixtures thereof; an anion selected from the group consisting of chlorine, bromine, iodine, and mixtures thereof; and a water soluble neutral amino acid wherein the molar ratio of total metal to said anion is less than about 1.3; the molar ratio of aluminum to non-aluminum metal is from about 2 to about 10; and the molar ratio of water soluble neutral amino acid to total metal is from about 0.09 to about 0.75; wherein said non-aluminum metal is incorporated into the antiperspirant complex in the form of a compound having the empirical formula $DO(OH)_{2-m}Y_m$ wherein m has a value of about 1.0, D is selected from the group consisting of zirconium, hafnium, and mixtures thereof, and Y is selected from the group consisting of chlorine, bromine, iodine, and mixtures thereof.

24. The complex of claim 23 wherein the molar ratio of aluminum to non-aluminum metal is from about 2.5 to about 4.5.

25. The complex of claims 23 or 24 wherein the molar ratio of total metal to said anion is from about 0.8 to about 1.25.

26. The complex of claims 23 or 24 wherein said non-aluminum metal and D are both zirconium and wherein said anion and Y are both chlorine.

27. The complex of claim 25 wherein said non-aluminum metal and D are both zirconium and wherein said anion and Y are both chlorine.

28. The complex of claims 23 or 24, wherein said water soluble neutral amino acid is glycine.

29. The complexes of claim 25 wherein said water soluble neutral amino acid is glycine.

30. The complex of claim 26 wherein said water soluble neutral amino acid is glycine.

31. The complex of claim 27 wherein said water soluble neutral amino acid is glycine.

* * * * *